United States Patent
Shaw

(10) Patent No.: US 6,297,245 B1
(45) Date of Patent: Oct. 2, 2001

(54) CISPLATIN AND FOLIC ACID ADMINISTERED TO TREAT BREAST CANCER

(75) Inventor: Jiajiu Shaw, Ann Arbor, MI (US)

(73) Assignee: Unitech Pharmaceuticals, Ann Arbor, MI (US)

( * ) Notice: Subject to any disclaimer, the term of this patent is extended or adjusted under 35 U.S.C. 154(b) by 0 days.

(21) Appl. No.: 09/358,803

(22) Filed: Jul. 21, 1999

Related U.S. Application Data

(60) Provisional application No. 60/096,700, filed on Aug. 4, 1998.

(51) Int. Cl.[7] .......................... A61K 31/495; A61K 31/50
(52) U.S. Cl. ............................ 514/252; 514/492; 544/261
(58) Field of Search ......................... 544/261; 23/305 R; 514/492, 252

(56) References Cited

U.S. PATENT DOCUMENTS

| 5,466,678 | * | 11/1995 | Kawabata et al. | 514/46 |
| 5,922,689 | * | 7/1999 | Shaw | 514/45 |
| 6,001,817 | * | 12/1999 | Shaw | 514/45 |
| 6,056,973 | * | 5/2000 | Allen et al. | 424/450 |

FOREIGN PATENT DOCUMENTS

| 09059288 | * | 3/1997 | (JP) . |
| 8802261 | * | 4/1988 | (WO) . |

OTHER PUBLICATIONS

Stewart et al., "Association of Cisplatin Nephrotoxicity with Patient Characteristics and Cisplatin Administration Methods," *Cancer Chemotherapy and Pharmacology*, 40(4), 293–308 (1997) including EMBASE abstract.*

Taylor et al., "Effects of cis–Dichloroammine Platinum (II) on DNA Synthesis in Kidney and Other Tissues of Normal and Tumour–Bearing Rats," *European Journal of Cancer*, 12(4), 249–254 (Apr. 1976).*

Berkow et al. (eds), *The Merck Manual for Diagnosis and Therapy*, 16th Edition, Merck & Co., Rahway, NJ, May, 1992, only p. 1280 supplied.*

Goodman & Gilman's *The Pharmacological Basis of Therapeutics*, 8th Edition, Gilman et al. (eds), Pergamon Press, Inc., New York, NY, 1990, only pp. 300–301 supplied.*

* cited by examiner

*Primary Examiner*—Gary Geist
*Assistant Examiner*—L. E. Crane
(74) *Attorney, Agent, or Firm*—Brinks Hofer Gilson & Lione

(57) ABSTRACT

A novel pharmaceutical composition, comprising cisplatin and folic acid is disclosed. The preparation of this pharmaceutical composition is also disclosed. The composition may be used to treat cancers and Acquired Immune Deficiency Syndrome (AIDS).

5 Claims, No Drawings

CISPLATIN AND FOLIC ACID ADMINISTERED TO TREAT BREAST CANCER

RELATED APPLICATIONS

Cross References to Related Applications

The present application claims priority to U.S. Provisional Application No. 60/096,700 filed on Aug. 4, 1998. In addition, the present application incorporates by reference the disclosures U.S. Pat. No. 5,922,689 and U.S. Pat. No. 6,001,817.

FEDERALLY SPONSORED RESEARCH OR DEVELOPMENT

There is no Federally sponsored research and development in this application.

BACKGROUND OF THE INVENTION

Cisplatin (cis-diamminedichloroplatinum, cis-Pt(NH$_3$)$_2$Cl$_2$, molecular weight 300.05) has been used as a chemotherapeutic agent for many years since the discovery of its anti-tumor activity by B. Rosenberg et al. (*Nature*, 1965, 205, 698; *Nature*, 1972, 222, 385).

The physician's Desk Reference (PDR) reports that cisplatin (the commercial name is Platinol®) can be used to treat testicular cancer, ovarian cancer, and bladder cancer.

Rosenberg et al., U.S. Pat. No. 4,177,263, describes methods of treating cancer using cisplatin and cisplatin analogs. The compounds were effective for treating leukemia and tumors induced in mice.

Chemical & Engineering News (Oct. 23, 1995) reported that "[Cisplatin] was first synthesized in the 1800s, but its anticancer activity was not discovered until the 1960s. In 1979, it was approved by the Food & Drug Administration for clinical treatment of testicular and ovarian tumors and cancers of the head and neck. Cisplatin and an analog, carboplatin, are now among the most widely used anticancer drugs."

After so many years, cisplatin is still being widely used because of its efficacy. However, its major drawback, the toxicity, is still a major concern.

Many attempts have been made to modify the cisplatin molecule in order to reduce its toxicity. Other attempts have been made to understand the interaction between cisplatin and DNA, which is the ultimate target of cisplatin. A few attempts have also been made to modify the composition of cisplatin dosage form to reduce its toxicity or improve its efficacy.

Many articles have been published which suggest modifying the composition of the dosage forms of cisplatin by combining it with other compounds. For example, cisplatin has been used in combination with caffeine by H. Yasutake et al. (*Gan to Kagaku Ryoho* 1989, 16, 2031–8) and by H. Tsuchiya (*Kanazawa Daigaku Juzen Igakkai Zasshi* 1988, 97, 543–56). Cisplatin has also been used in combination with cytosine arabinoside and the combination has shown some advantages as shown by J. Berek et al. (*Obstet. Gynecol.* 1989, 74, 663–6). Another combination, cisplatin and novobiocin, has also been shown to be advantageous by P. Eder et al. (Cancer Research 1989, 49 595–8, U.S. Pat. No. 5,130,145). This prior art indicates that when cisplatin and L-ascorbic acid are administered simultaneously, the anti-tumor activity is higher.

None of these prior arts suggest or disclose using folic acid along with cisplatin in a pharmaceutical composition for cancer therapy. This may be because folic acid has not been used as a conventional pharmaceutical excipient.

BRIEF SUMMARY OF THE INVENTION

This invention comprises a novel pharmaceutical composition comprising cisplatin and folic acid. Optionally, pharmaceutical excipients can be present.

This composition is different from the conventional pharmaceutical compositions, which do not contain folic acid.

Predominantly, cisplatin binds onto deoxyguanosine of DNA. However, cisplatin also binds onto other deoxynucleosides or nucleosides. Because of the non-selectivity of cisplatin, it can cause lots of side effects. Therefore, reducing the toxicity of cisplatin is a very important issue. In this invention, the novel composition comprising cisplatin and folic acid has been surprisingly demonstrated to be less toxic under lower calcium concentration. This results indicate that the novel composition has a broader dosage range than cisplatin at physiologic calcium concentration. Therefore, this invention is a better pharmaceutical composition than current cisplatin compositions.

Because cisplatin binds onto DNA or RNA, this composition may also be used to treat viruses, such as Human Immunodeficiency Virus (HIV), to bind its DNA or RNA and kill the virus. Thus, the composition may be used for the treatment of Acquired Immune Deficiency Syndrome (AIDS) patient. The composition may also be used in combination with other well known AIDS drugs, such as 3'-azidothymidine (AZT), to interfere with the HIV enzyme reverse transcriptase and achieve the goal of hampering the reproduction of HIV.

DETAILED DESCRIPTION OF THE INVENTION

This invention comprises a novel pharmaceutical composition comprising cisplatin and folic acid. Said pharmaceutical composition has a mole ratio between cisplatin and folic acid in the range of about 1:0.05 to 1:1, preferably 1:0.1 to 1:0.8, most preferably 1:0.2 to 1: 0.5.

Cisplatin is commercially available from many sources such as Sigma Chemical Company and Alfa Aesar. Folic acid is also commercially available from a variety of sources such as Spectrum Quality Products, Inc. and Sigma Chemical Company.

The composition of the present invention may optionally include other pharmaceutically acceptable excipients. Suitable pharmaceutical excipients are customary and physiologically acceptable such as sodium bicarbonate, mannitol, lactose, sodium chloride, phosphates, water, ethanol, hydrochloric acid, magnesium stearate, cellulose, starch, polyethylene glycol, etc. Therefore, the composition may be in a liquid or solid dosage form suitable for parenteral or oral administration to a patient.

The method of preparing the composition comprises the following:

(1) Combining cisplatin and folic acid in a solvent at a molar ratio of about 1:0.05 to 1:1 so that the percentage of cisplatin is 0.005% to 0.25% in the aliquot, whereas said solvent is water containing suitable amount of sodium bicarbonate, 0.1% to 99% methanol in water, 0.1% to 99% ethanol in water, 0.1% to 99% acetone in water, 0.05% to 5.0% sodium chloride in water, 0.0001 N to 1.0 N hydrochloric acid, or a mixture of said solvents.

(2) Stirring the aliquot until it becomes a solution.

(3) Filtering through a filter, preferably a filter with a porosity of between 0.1 μm to 1.0 μm, more preferably between 0.2 μm to 0.45 μm and collecting the filtrate.

(4) Optionally, drying the filtrate from step (3) under vacuum or by other standard pharmaceutical techniques.

(5) Optionally, reconstituting the dried composition from step (4) into a solution or a suspension by a suitable solvent. Typically, the percentage of cisplatin is 0.005% to 0.25%, preferably 0.01% to 0.1%. Suitable solvents include water containing sodium bicarbonate, ethanol, 0.1% to 90% ethanol in water, 0.05% to 5.0% sodium chloride in water, 0.0001 N to 1.0 N hydrochloric acid, or a mixture of said solvents.

(6) Optionally, blending the dried composition from step (4) with one or more physiologically acceptable pharmaceutical excipient(s). The resulting product can be encapsulated or compressed into capsules or tablets using standard pharmaceutical techniques.

This invention may be used to treat all cancers that may be treated by cisplatin. They include testicular cancer, ovarian cancer, bladder cancer, leukemia, and cancers of the head and neck. This invention may also be used to treat breast cancer as indicated by the in-vitro studies in example 4.

Another part of this invention is related to the method for treating cancer patients by this composition. The composition may be administered to a cancer patient orally, or by subcutaneous or intravenous injection, or by means of an implanted reservoir, or by means of applying on the cancerous skin.

The injectable compositions are normally in the form of an aqueous solution. If necessary, pharmaceutically-acceptable suspensions can be employed. Typically, such a solution contains cisplatin at a concentration of about 0.005%–0.25% (0.05 mg/mL–2.5 mg/mL), more commonly about 0.01%–0.1% (0.1 mg/mL–1 mg/mL). The dosage administered by injection comprises cisplatin in the range of about 5–1,000 mg in the first day of every 1–4 weeks depending upon the patient. Typically, one might administer a dosage of about 50–400 mg in the first day of every 1–4 weeks to a patient having a body weight of about 40–100 kg, although in appropriate cases such dosages may prove useful for patients having a body weight outside this range.

The composition may also be administered orally, for example, as a solution or a suspension or as tablets or capsules. Solution and suspension for oral administration are typically of about the same concentration as those used for injection. However, when administering the drug orally, it may be desirable to use a higher dosage rate than when administering it by injection. For example, a dosage containing about 10–1,500 mg cisplatin in the first day of every 1–4 weeks may be used. Typically, one might administer a dosage containing about 50–600 mg cisplatin in the first day of every 1–4 weeks. In preparing such tablets or capsules, standard tablet or capsule making techniques may be employed. If desired, suitable pharmaceutically acceptable excipients such as starch, mannitol, cellulose or lactose may be used in preparing the tablets or capsules. Capsules may also be prepared using soft gelatin as the encapsulating agent. If desired, such capsules may be in the form of sustained release capsules wherein the main capsule contains microcapsules which release the active ingredient over a period of several hours.

This composition may also be used in the treatment of AIDS. Because of the ability of cisplatin to hamper the DNA or RNA replication process, it is likely that this composition will also be effective against the HIV and may be used for the treatment of AIDS. It may also be used in combination with other well known AIDS drugs, including but not limited to AZT, to interfere with the HIV enzyme reverse transcriptase and achieve better results.

This composition may be administered to an AIDS patient in the same way as in the treatment of a cancer patient. A composition having about 10–600 mg of cisplatin in the first day of every 1–4 weeks may be administered.

When used in conjunction with a well known drug for AIDS, such as AZT, the dosage of cisplatin in the composition may be suitably reduced. A composition having 5–1, 500 mg of cisplatin in the first day of every 1–4 weeks may be administered; the dosage and the method of administration of said drug for AIDS is the same as it is normally used.

EXAMPLES

Several examples of the composition are shown as follows:

EXAMPLE 1

Composition in accordance with present invention

1. Weigh 30 mg of cisplatin (about 0.2 mmole).
2. Weigh 250 mg of folic acid (containing 8.5% water) (about 0.1 mmol).
3. Weigh 500 mg of sodium bicarbonate.
3. Add the weighed cisplatin, folic acid, and sodium bicarbonate into 500 mL of water.
4. Stir the aliquot for 30 minutes or until it becomes a solution.
5. Filter the solution through a suitable filter with a porosity of 0.2 μM and collect the filtrate.

The final liquid composition has a cisplatin concentration of about 06% and the mole ratio of cisplatin and folic acid is about 1:0.5.

EXAMPLE 2

1. Weigh 30 mg of cisplatin (about 0.2 mmole) and add it into 200 mL of water.
2. Weigh 250 mg of folic acid (about 0.1 mmole) and add it into 300 mL of water containing 600 g of sodium bicarbonate.
3. Mix the two aliquots from step 1 and from step 2 in a suitable container.
4. Stir the aliquot (from step 3) overnight.
5. Filter the solution through a suitable filter with a porosity of 0.2 μM and collect the filtrate.
6. Dry the filtrate by a rotary evaporator or other standard pharmaceutical techniques.

The final solid composition has a mole ratio of cisplatin acid of about 1:0.5.

EXAMPLE 3

1. Weigh 100 g of the dry composition made according to the procedures in Example 2; add it into 300 g of lactose; mix until the blend is uniform.
2. Add the blend made from step 1 into 400 g of mannitol and mix well.
3. Add 10 g of magnesium stearate into the blend made from step 2 and mix for three minutes.
4. Encapsulate the blend from step 3 into suitable capsules so that each capsule contains 100 mg of cisplatin.

The final composition in each capsule contains 100 mg cisplatin and the mole ratio of cisplatin folic acid.

EXAMPLE 4

The composition prepared according to Example 1 (identified as #801C) and cisplatin were evaluated, side by side, for their biologic activities against human breast cancer cells (MCF-7) and against normal human mammary cells (NHMC). The results shown the extent of inhibition of cell growth compared to controls expressed in percent inhibition. The results are shown as follows:

Table 1 Percent Growth Inhibition in MCF-7 Cells.

TABLE 1

Percent Growth Inhibition in MCF-7 Cells

|  | 25 µL | 10 µL | 5 µL |
| --- | --- | --- | --- |
| by cisplatin | 92% | 49% | 25% |
| by #801C | 83% | 44% | 34% |

The inhibitions on MCF-7 are essentially the same for cisplatin and #801C.

Table 2 Percent Growth Inhibition in NHMC Cells Grown in RPMI-10.

TABLE 2

Percent Growth Inhibition in NHMC Cells Grown in RPMI-10

|  | 1/100 | 1/200 | 1/400 |
| --- | --- | --- | --- |
| by cisplatin | 88% | 46% | 0% |
| by #801C | 67% | 31% | 20% |

RPMI-10 refers to standard RPMI-1640 medium with 10% fetal calf serum added. The inhibitions on NHMC are not significantly different for cisplatin and #801C.

Table 3 Percent Growth Inhibition in NHMC Cells Grown at Low Calcium Concentration (40 µM).

TABLE 3

Percent Growth Inhibition in NHMC Cells Grown at Low Calcium Concentration (40 µM)

|  | 1/100 | 1/200 | 1/400 |
| --- | --- | --- | --- |
| by cisplatin | 32% | 31% | 27% |
| by #801C | 24% | 13% | 1% |

The inhibition of #801C on NHMC is significantly lower than that of cisplatin indicating that #801C may be less toxic than cisplatin under a physiologic condition with lower calcium concentration.

In conclusion, this invention comprises a novel pharmaceutical composition of cisplatin, the preparation, and the use of said composition for the treatment of cancer and AIDS.

Although the description above contains many specificities, these should not be construed as limiting the scope of the invention but as merely providing the illustrations of some of the presently preferred embodiments of this invention.

Thus the scope of this invention should be determined by the appended claims and their legal equivalents, rather than by the examples given.

I claim:

1. A method of treating breast cancer, comprising administering a therapeutically effective amount of a pharmaceutical composition comprising cisplatin and folic acid, wherein said pharmaceutical composition has a mole ratio of cisplatin to folic acid in the range of about 1:0.05 to 1:1., to a patient in need thereof wherein the composition is administered parenterally and contains between 5 and 1,000 mg of cisplatin, and is administered in the first day of every 1 to 4 weeks.

2. The method of claim 1 wherein the composition contains between 50 and 400 mg of cisplatin.

3. A method of treating breast cancer, comprising administering a therapeutically effective amount of a pharmaceutical composition comprising cisplatin and folic acid, wherein said pharmaceutical composition has a mole ratio of cisplatin to folic acid in the range of about 1:0.05 to 1:1., to a patient in need thereof wherein the composition is administered orally and contains between 10 and 1,500 mg of cisplatin and is administered in the first day of every 1 to 4 weeks.

4. The method of claim 3 wherein the composition contains between 50 and 600 mg of cisplatin.

5. A method of treating breast cancer, comprising administering a therapeutically effective amount of a pharmaceutical composition comprising cisplatin and folic acid, wherein said pharmaceutical composition has a mole ratio of cisplatin to folic acid in the range of about 1:0.05 to 1:1.

* * * * *